United States Patent [19]

Houben

[11] Patent Number: 6,143,821

[45] Date of Patent: Nov. 7, 2000

[54] WATER-ABSORBING POLYMERS WITH IMPROVED PROPERTIES, PROCESS FOR THE PREPARATION AND USE THEREOF

[75] Inventor: Jochen Houben, Kempen, Germany

[73] Assignee: Stockhausen GmbH & Co. KG, Krefeld, Germany

[21] Appl. No.: 09/068,560

[22] PCT Filed: Nov. 18, 1996

[86] PCT No.: PCT/EP96/05074

§ 371 Date: May 20, 1998

§ 102(e) Date: May 20, 1998

[87] PCT Pub. No.: WO97/18890

PCT Pub. Date: May 29, 1997

[30] Foreign Application Priority Data

Nov. 21, 1995 [DE] Germany ............................ 195 43 368

[51] Int. Cl.$^7$ .................................................. C08L 29/04
[52] U.S. Cl. ............................................................. 524/557
[58] Field of Search .............................................. 524/557

[56] References Cited

U.S. PATENT DOCUMENTS

| | | | |
|---|---|---|---|
| 4,618,703 | 10/1986 | Thanawalla et al. | 560/209 |
| 4,906,717 | 3/1990 | Cretenot et al. | 526/209 |
| 5,154,713 | 10/1992 | Lind | 604/358 |
| 5,314,420 | 5/1994 | Smith et al. | 604/358 |

FOREIGN PATENT DOCUMENTS

WO 94/09043  4/1994  WIPO .

*Primary Examiner*—Terressa Mosley
*Attorney, Agent, or Firm*—Oblon, Spivak, McClelland, Maier & Neustadt, P.C.

[57] ABSTRACT

The present invention relates to powdery absorbents for water and aqueous liquids, which are based on water-swellable, but not water-soluble, polymers, are cross-linked, and are built up of partially neutralized, monoethylenically unsaturated, acid groups-containing monomers, optional further monomers copolymerizable with these, and optional polymers suitable as a graft basis. These polymers are produced by using a cross-linker combination consisting of $$CH_2=CR^5-CO-(OCHR^3-CHR^3)_z O-CH_2-CR^5=CH_2 \qquad \text{I.}$$

$$R^1-[O(CHR^3-CHR^3O)_u-CO-R^2]_x \qquad \text{II.}$$

with

R$^1$: multivalent C$_{2-10}$-alkyl,

R$^2$: linear or branched C$_{2-10}$-alkenyl,

R$^3$: H, CH$_3$, C$_2$H$_5$,

R$^5$: H, CH$_3$, x: 2–6, u: 0–15, z: 3–20 and a secondary cross-linker. Superficial secondary cross-linkage achieves a property combination of high retention, high absorption under pressure, low soluble contents, and a rapid liquid absorption. The polymers are used in constructions, such as diapers, for the absorption of body fluids, in current-conducting or light-transmitting cables, and in the cultivation of plants.

23 Claims, No Drawings

WATER-ABSORBING POLYMERS WITH IMPROVED PROPERTIES, PROCESS FOR THE PREPARATION AND USE THEREOF

The present invention relates to powdery absorbents for water and aqueous liquids based on water-swellable, but not water-soluble polymers. These cross-linked polymers based on acid groups-containing monomers are obtained by using a special combination of two precross-linking agents and one secondary cross-linking agent. They show property combinations of high retention, high absorption under pressure, low soluble constituents, and rapid liquid absorption, which have not been achieved as yet.

Commercially available superabsorbent polymers are mainly cross-linked polyacrylic acids or cross-linked starch/acrylic acid-graft copolymers wherein the carboxyl groups are partially neutralized with sodium or potassium ions.

These polymers are used, for example, in hygienic articles capable of absorbing body fluids, such as urine, and in materials to sheathe cables. Here, they absorb large amounts of aqueous liquids and body fluids, such as urine or blood, under swelling and formation of hydrogels. Additionally, it is necessary to retain the absorbed liquid amount under the typical pressure during application. While advancing superabsorbent polymers, the requirements made on these products have substantially changed in the last years. Initially, only the very high swelling capacity on contact with liquids had been the main factor in the development of superabsorbers; however, it was found later that, in addition to the absorbed liquid amount, the stability of the swollen gel is also of importance. However, retention on the one hand, and stability of the swollen gel on the other one, represent contrary properties, as has been known from U.S. Pat. No. 3,247,171. This means that polymers having a particularly high retention only have a poor rigidity of the swollen gel with the result that the gel is deformable under an exerted pressure (e.g., body load) and therefore impairs further liquid absorption. This specific absorption property, which is referred to as "absorption under pressure" (AUP) in the Anglo-Saxon usage, is described in U.S. Pat. No. 5,314,420, for example. With the increasing requirements made on superabsorbers in the hygienic field, it was found that the initial load of 21 g/cm2 (0.3 psi) no longer corresponded to the desired property standard necessary for incontinence products or diaper constructions with low fluff contents and large amounts of superabsorber. For this reason, pressure loads of 49 g/cm2 (0.7 psi) are demanded today.

Although the skilled artisan is familiar with methods of producing products having, for example, a high retention or a high absorption or low soluble constituents or a rapid water absorption, achieving all of these four positive properties at the same time has not been possible with formulations known as yet. For example, it is well known to the skilled artisan that increasing the cross-linker concentration results in products with a low soluble content. However, this also results in products having a poor retention. Decreasing the cross-linker concentration, on the other hand, results in products with a high retention, but also with high soluble constituents and, due to gel blocking, with slow water absorption.

The effort to obtain products with high gel volume, high gel stability, and low soluble constituents, which is described in U.S. Pat. No. Re 32,649, resulted in the desired product properties only when the cross-linking agent methylenebisacrylamide which splits off the carcinogenic acrylamide was used. For this reason, it is not possible to use such products in hygienic articles.

Along with a high level of retention and liquid absorption under pressure, the content of soluble polymer chains in the superabsorbers must be as low a possible. These arise as a result of incomplete cross-linkage during polymerization. In use these soluble constituents are incompletely retained in the swollen polymer body. This results in reduced superabsorber performance because of nonuniform liquid distribution in the diaper; moreover, in extreme cases, these soluble constituents can escape from the diaper construction, causing a slimy feeling on the skin. According to the teaching of EP 312 952, good stability of the swollen gel, high absorption rate, and high water absorption absolutely require low soluble components in the polymer. U.S. Pat. No. Re 32,649, for example, mentions as limit values for low soluble contents 17% after 16 hours; but this must be regarded as too high because of the drift toward thinner diapers with a higher superabsorber portion per diaper. A value of 12%, or better of 10%, after 16 hours should be realized in modern superabsorbers.

Another requirement made on superabsorbers in such sanitary articles with reduced fluff portion and increased superabsorber portion is the property of rapidly absorbing liquids at the moment of occurrence, because the buffer effect of the fluff pulp portion is considerably reduced. U.S. Pat. No. 5,314,420 teaches a method of producing a rapid-absorbing superabsorber by adding sodium carbonate. This measure obviously only results in a physical structural change of the superabsorbers causing a faster suction rate; however, the other basic properties of the polymer are not improved. Treating the surface with a surfactant-like material to increase the water absorption rate—as is described in WO 93/24153—fails because of the rewet behavior, that is, the superabsorbent polymer's property of storing once absorbed liquids permanently, which is so important in practice. The presence of surfactants considerably impairs this property.

The object of WO 94/09043 is to provide new superabsorbent polymers having an increased absorption capacity for aqueous liquids, even under pressure load. To achieve this object, it describes double-cross-linked superabsorbers which are produced in a first step by precross-linkage during polymerization with methylenebisacrylamide, bis(acrylamido) acetic acid, allyl acrylate, allyl methacrylate, esters or amides with terminal vinyl and allyl functions, or with highly ethoxylated trimethylolpropane triacrylate; in the second step, the surface of the resultant polymer particles is coated with a cross-linker, followed by cross-linking. In this process, which is known per se, the preferred surface cross-linking agents are polyhydroxy compounds which are applied together with water or water/solvent mixtures and reacted at elevated temperatures (175–230° C.), after the moisture of the polymer gel from the first step has partially been removed.

It is said that combining one of the mentioned primary cross-linkers with the secondary surface cross-linkers achieves unique product properties with respect to retention and liquid absorption under pressure, providing the advantageous application in hygienic articles wherein the absorbent polymers have to absorb large amounts of liquid and retain them even under pressure load. However, these products do not meet the important demand on modern diaper constructions for rapid liquid absorption.

WO 93121237 describes superabsorbent polymers that are cross-linked with unsaturated esters of polyalkyl glycols; in a subsequent heating process their properties are improved with respect to retention and liquid absorption under a low pressure of 21 g/cm2 (0.3 psi) to 25 g/g.

Ethoxylated trimethylolpropane triacrylate is the preferred cross-linker, and the number of EO-units per polyglycol chain may be in the range of 2 to 7. According to the statements in this publication, superabsorbers cross-linked with non-ethoxylated or only slightly ethoxylated trimethylolpropane triacrylate exhibit poor properties. The described products do not meet today's requirements with respect to absorption under a higher load of 49 g/cm2 (0.7 psi). FIG. 13 on page 8/8 of WO 93/21237, which represents the course of liquid absorption under pressure for various pressure loads, clearly shows the deficiency of the described polymers, the measured values of about 18 g/g in the interesting pressure load range of 63 g/cm2 (0.9 psi) are absolutely unsatisfactory. This applies all the more so since the measured values have been established with an absolutely unusual screening fraction of 300–600 $\mu$m, which per se results in higher measuring values than the screening fraction of 150–800 $\mu$m which is common in practice.

It is the object of U.S. Pat. No. 5,314,420 to provide products that are capable of absorbing liquids very rapidly. This is achieved by adding a carbonate-containing blowing agent to the monomer solution and subsequent re-cross-linkage of the formed polymer. This publication mentions the possibility of combining several preferred cross-linking agents; however, there is no solution for the problem of simultaneously increasing retention, absorption under pressure, and absorption rate, as well as that of reducing the soluble contents.

It has not been possible with the products manufactured so far to combine the properties high retention, high absorption under pressure, and rapid liquid absorption with simultaneously low soluble contents.

Another problem in the production of superabsorbent polymers is the relatively poor solubility of many standard cross-linkers in the aqueous monomer solution at the low temperatures of, e.g., well below 20° C. in the beginning of polymerization. Using usual cross-linkers, such as, trimethylolpropane triacrylate, diethylene glycol diacrylate, tetraethylene glycol dimethacrylate, or allyl methacrylate, to mention only a few examples, the aqueous monomer solution becomes cloudy at these temperatures. This turbid solution points out that the cross-linking agents are not dissolved homogeneously, resulting in nonuniform cross-linkage during subsequent polymerization and thus in a substandard product.

To evade this problem, DE-OS 41 38 408 proposes to add to the monomer solution a surfactant that cannot be incorporated by polymerization, so that the otherwise poorly soluble cross-linking agent is distributed more evenly. However, this method has two major disadvantages. On the one hand, when the surfactant-containing monomer solution is blown off with nitrogen it foams to such an extent that blowing carried out to remove the disturbing oxygen from the monomer solution lasts longer than without surfactant addition. On the other hand, surfactants in the polymer favor escape of the absorbed water, resulting in the undesired phenomenon of rewet, and disqualifying the product for the use in hygienic articles because it releases absorbed liquids too easily.

WO 93/21237 gives another solution for the described problem; here (meth)acrylic acid esters of highly ethoxylated polyglycols are used as cross-linking agents, ethoxylated trimethylolpropane being preferred. Depending on the ethoxylation degree, these products are soluble in the monomer solution and therefore distributed uniformly, resulting in products having the desired low soluble content. However, the disadvantage of these cross-linking agents is that the re-cross-linked product does not have retentions of above 30 g/g, and that the absorption under pressure (21 g/cm²) does not exceed a value of 28 g/g (cf. Table 1). It is not possible to use non-ethoxylated or only slightly ethoxylated cross-linking agents because they cause bad values in these systems, in particular concerning soluble constituents. Moreover, this publication offers no solution regarding an improvement of the suction force of the absorber.

It is accordingly the object of the present invention to provide for the production of superabsorbent polymers cross-linking agents or combinations of cross-linking agents which are soluble in the monomer solution without any auxiliary agents and result in a good retention and absorption under pressure in re-cross-linked polymers and simultaneously in low soluble constituents of less than 12% (16 h-value), thereby providing products having a rapid water absorption. At the same time, cross-linkers should be omitted that split off the carcinogenic acrylamide, such as methylene-bisacrylamide, or which may cause sensitization, such as ethylene glycol dimethacrylic acid esters.

Most surprisingly, it was found that superabsorbers that are based on acid groups-containing monomers and which are produced by a combination of two different precross-linking agents I and II, known per se,

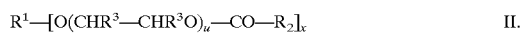

with
$R^1$: multivalent $C_{2-10}$-alkyl,
$R^2$: linear or branched $C_{2-10}$-alkenyl,
$R^3$: H, $CH_3$, $C_2H_5$,
$R^5$: H, $CH_3$,
x: 2–6,
u: 0–15,
z: 3–20 and subsequent re-cross-linkage with a secondary cross-linker result in products which have a retention of above 30 g/g, an absorption under pressure of above 20 g/g, soluble contents (16 h) of below 12%, and at the same time a rapid liquid absorption, expressed by a swelling rate of below 40 sec.

The preliminary cross-linking agent I, a (meth)acrylic acid ester of a polyglycol mono(meth)allyl ether, comprises a (meth)allyl function, a (meth)acrylic acid ester function, and a hydrophilic chain inserted between these two functions and consisting of at least 3, preferably 5 to 20, most preferably 8–12 glycol units. Suitable glycol units include both ethylene glycol and propylene glycol units, individually or mixed; in case of mixtures both random and block alkoxylates are suitable. It is possible to use both mixed ethylene glycol/propylene glycol chains and pure propylene glycol chains, pure polyethylene glycol chains being preferred.

The described precross-linking agents of type I may be produced, for example, according to the method described in U.S. Pat. No. 4,618,703, or by direct esterification with an excess of acrylic acid or methacrylic acid (Examples 4–9). The esters so obtained may be stored in crude condition, i.e., in the presence of the used catalyst and the (meth)acrylic acid used in excess, and then be further processed. If a higher purity is required or for reasons of longer storage, it is also possible to wash the esters and purify them from low-boiling components by distillation, as is described in U.S. Pat. No. 4,618,703. The degree of esterification should be above 90, or better above 95%, since free hydroxyl functions initially do not improve the technological properties and result in a reduction of retention during subsequent re-cross-linkage.

The precross-linking agent II, a (meth)acrylic acid ester of polyhydroxy compounds, is a multifunctional alcohol whose alcohol functions have been converted into (meth)acrylic acid esters. Suitable polyhydroxy compounds include, for example, trimethylolpropane, ethylene glycol, propylene glycol, glycerol, pentaerythritol, or their ethoxylated homologues, such as polyethylene glycol. Esters wherein part of the hydroxyl groups has remained unesterified, as may be the case in technical products, are also included. It is in particular also possible to use as cross-linking agent II (meth)acrylic acid esters which are normally poorly soluble in the monomer solution, such as trimethylolpropane triacrylate, trimethylolpropane-3EO-triacrylate, ethylene glycol diacrylate, diethylene glycol dimethacrylate, since these are kept in solution by cross-linker I.

The precross-linking agents of type II are commercially available. Craynor CN 435 used in the Examples is the triacrylic acid ester of 15-EO-trimethylolpropane; Craynor SR 351 is the triacrylic acid ester of trimethylolpropane. Both products are manufactured by Cray-Valley-Company.

Precross-linking agent I is used in amounts of 40–90, preferably 40–80, and most preferably 60–80 mole percent, relative to the mixture of cross-linkers, and precross-linking agent II in amounts of 10–60, preferably 20–60, and most preferably 20–40 mole percent, relative to the cross-linker mixture. With respect to the unsaturated acid monomer component, this cross-linker combination is used in concentrations of 0.1–2%, preferably 0.3–1.0%-wt.

Taken alone, both types of cross-linking agents are known to the average skilled artisan for the production of cross-linked polyacrylates. In particular, the possibility of using (meth)acrylic acid esters of polyglycol monoallyl ethers is mentioned in U.S. Pat. Nos. 4,076,663, 4,654,039, 4,906,717, 5,154,713, and 5,314,420. However, the advantageous combination of precross-linking type I with precross-linking type II is not mentioned in U.S. Pat. No. 4,654,039, U.S. Pat. No. 5,154,713, U.S. Pat. No. 5,314,420, and U.S. Pat. No. 4,076,663. Only U.S. Pat. No. 4,906,717 mentions the possibility of combining several types of cross-linking agents, a vast list also includes the ones according to the present invention; however, the advantages of such a combination are not disclosed, and there are no embodiment examples. In particular, the advantages of this cross-linker combination combined with the secondary cross-linkage according to the present invention are neither mentioned nor recognized.

The described cross-linker combination has the surprising advantage that even poorly soluble cross-linker components II are solubilized by the presence of I, and that they can therefore fully develop their activity without impairing the rewet behavior owing to the presence of surfactants which are not incorporated by polymerization, as is the case in DE 41 38 408.

The method of secondary surface cross-linkage improves the characteristics of the superabsorbers according to the present invention, in particular with respect to their liquid absorption under pressure, since the known phenomenon of "gel blocking" is suppressed where swollen polymer particles stick together and thus impair further liquid absorption and liquid distribution within the diaper. During secondary cross-linkage the carboxyl groups of the polymer molecules are cross-linked at the surface of the superabsorber particles with cross-linking agents at elevated temperatures. Methods for secondary cross-linkage according to the present invention are described in several publications, for example, DE 40 20 780, EP 317 106, and WO 94/9043. All of the secondary cross-linking agents known to the skilled artisan, for example, from U.S. Pat. No. 5,314,420, page 8, lines 3–45, can advantageously be used according to the present invention in combination with precross-linker combination I and II. These compounds generally comprise at least two functional groups. Alcohol, amine, aldehyde, glycidyl, and epichloro functions are preferred, but cross-linker molecules having several different functions may also be used. Preferably, one of the following secondary cross-linking agents is used: ethylene glycol, diethylene glycol, triethylene glycol, polyethylene glycol, glycerol, polyglycerol, propylene glycol, diethanolamine, triethanolamine, polypropylene oxide, block copolymers of ethylene oxide and propylene oxide, sorbitan fatty acid esters, ethoxylated sorbitan fatty acid esters, trimethylolpropane, ethoxylated trimethylolpropane, pentaerythritol, ethoxylated pentaerythritol, polyvinyl alcohol, sorbitol, ethylene carbonate, propylene carbonate, and polyepoxides, such as ethylene glycol diglycidyl ether. It is particularly preferable to use ethylene carbonate as secondary cross-linking agent. The secondary cross-linking agent is used in an amount of 0.01 to 30 percent by weight, preferably 0.1–10 percent by weight, and most preferably 0.1–1 percent by weight, relative to the polymer to be re-cross-linked.

The polymerization process according to the present invention may be initiated by different conditions; for example, irradiation with radioactive, electromagnetic, or ultraviolet rays, or by redox reaction of two compounds, for example, sodium hydrogensulfite with potassium persulfate or ascorbic acid with hydrogen peroxide.

Thermally induced decomposition of a so-called radical starter, such as, azobisisobutyronitrile, sodium persulfate, t-butyl hydroperoxide, or dibenzoyl peroxide, may also be used to start polymerization. Additionally, it is possible to combine several of the above-mentioned methods. According to the present invention polymerization is preferably started by the redox reaction between hydrogen peroxide and ascorbic acid, and is completed by thermally induced decomposition of sodium persulfate and/or 2,2'-azobis(2-methylpropionamide) dihydrochloride.

Several methods are suitable to polymerize the superabsorbers according to the present invention; for example, bulk polymerization, solution polymerization, spray polymerization, inverse emulsion polymerization, and inverse suspension polymerization. It is preferable to carry out a solution polymerization in water used as solvent. Solution polymerization may be carried out either continuously or discontinuously. Patent literature gives a wide spectrum of variations concerning concentration ratios, temperatures, kind and amount of initiators and of secondary catalysts. Typical methods are described in the following patent documents which are incorporated in the production method according to the present invention by reference: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818.

The unsaturated, acid groups-containing monomers to be used according to the present invention include, for example, acrylic acid, methacrylic acid, crotonic acid, isocrotonic acid, maleic acid, fumaric acid, itaconic acid, vinylsulfonic acid, 2-acrylamido-2-methyl-1-propane sulfonic acid, vinyl acetic acid, methallyl sulfonic acid, as well as their alkali and/or ammonium salts. Up to 40%-wt. of further comonomers, relative to the acid monomers, for example, acrylamide, methacrylamide, and or their salts, may optionally be used to modify the polymer properties. It is additionally possible to use combinations of the above-mentioned monomers, as well as combinations of the above-mentioned monomers with nonionic hydrophilic monomers, such as, (meth)allyl alcohol, and the mono(meth)acrylic acid esters of multivalent alcohols or ethoxylates. It is also possible to use (meth)acrylonitrile, vinyl pyrrolidone, hydroxyethyl acrylate, and vinyl acetamide. However, it is preferable to use acrylic acid, methacrylic acid or their alkali or ammonium salts. Acrylic acid and its sodium and/or potassium salt is particularly preferred.

In the polymerization method according to the present invention the acid monomers may be neutralized by different manners. On the one hand, it is possible to carry out the polymerization according to the teaching of U.S. Pat. No. 4,654,039, that is, directly with the acid monomers and to effect neutralization subsequently in the polymer gel. Secondly and preferably, the acid monomer components are neutralized prior to polymerization to the extent of 25–95%, preferably 50–80%, and are then present as sodium and/or potassium and/or ammonium salts already at the beginning of polymerization.

For neutralization purposes it is preferable to use bases that do not have a negative influence on the polymerization carried out in a later stage. Preferably, sodium or potassium hydroxide solution and/or ammonia, most preferably sodium hydroxide solution, are used, and adding sodium carbonate, potassium carbonate, or sodium bicarbonate may have an additional positive effect, as is described in U.S. Pat. No. 5,314,420 and U.S. Pat. No. 5,154,713. In the case of adiabatic solution polymerization, this partially neutralized monomer solution is cooled to a temperature of below 30° C., preferably below 20° C., prior to starting the polymerization. If the other mentioned methods are used, other temperatures are known and usual in the art.

The polymers according to the present invention may comprise water-soluble polymers as graft basis in amounts of up to 30%-wt., relative to the sum of present monomers. Among others, these include partially or completely saponified polyvinyl alcohols, starch or starch derivatives, cellulose or cellulose derivatives, polyacrylic acids, polyglycols, or their mixtures. The molecular weights of the polymers added as graft basis must be adapted to the circumstances of the polymerization conditions. In the case of an aqueous solution polymerization, it may, for example, be necessary to use only low- or medium-molecular polymers due to the viscosity of the polymer solution, while this factor is of minor importance in suspension polymerization.

In addition to polymers obtainable by cross-linking polymerization of partially neutralized acrylic acid, those are preferably used which additionally comprise portions of graft polymerized starch or of polyvinyl alcohol.

In the end product, the acid monomers are neutralized to the extent of at least 25 mol-%, preferably at least 50 mol-%, and most preferably 50 to 80 mol-%. Neutralization is effected either by adding the corresponding alkali or ammonium hydroxides, or with the corresponding carbonates or hydrogen carbonates. Partial neutralization may also be effected during the production of the monomer solution, i.e., prior to polymerization, or, as described in U.S. Pat. No. 4,654,039, with the finished polymer. It is preferable to carry out the partial neutralization prior to polymerization.

The resultant polymer is dried, ground, and screened out to the size fraction favorable for incorporating it into disposable diapers, cable insulations or other products, and is then subjected to the secondary cross-linking reaction. In some cases, however, it has also proved successful to add the secondary cross-linking agents already before drying the polymer gel or before comminuting the partially or substantially dry polymer. A secondary cross-linkage to be carried out according to the present invention is described, for example, in U.S. Pat. No. 4,666,983 and DE 40 20 780. It is often advantageous to add the secondary cross-linkers as a solution in water, organic solvents or their mixtures, in particular when small amounts of a secondary cross-linking agent are used. Suitable mixers to apply the secondary cross-linking agent include, for example, Patterson-Kelley-mixers, DRAIS-turbulent mixers, Lödige-mixers, Ruberg-mixers, screw mixers, pan mixers, and fluidized-bed mixers, as well as continuous vertical mixers wherein the powder is mixed at high speed by means of rotary knives (Schugi-mixers). After mixing the secondary cross-linker with the precross-linked polymer, heating to temperatures of 120 to 250° C., preferably to 135 to 200° C., and most preferably to 150 to 185° C., is effected to carry out secondary cross-linkage. The point at which the desired property characteristics of the superabsorber are destroyed again because of heat damage limits the afterheating time.

Depending on their intended application, differing screening fractions are used to process the superabsorbers, for example, for diapers between 100 and 1,000 mm, preferably between 150 and 850 mm. This size fraction is generally produced by grinding and screening prior to secondary cross-linkage.

The hydrophilic superabsorbers according to the present invention are used wherever aqueous liquids are to be absorbed. These include, for example, the known applications of these products in hygienic articles in the form of diapers for babies and incontinence products for adults, sanitary napkins, wound patches, food packages; in agriculture in the cultivation of plants, cable insulation, absorbent sheet materials made of paper, water-soluble polymers and thermoplastic materials and foams; and as active substance carriers with a retarded release to the environment.

The examples that follow will demonstrate the manufacture of the cross-linking agents to be used according to the present invention, and they will further illustrate the production and properties of the polymers according to the present invention; the chapter "Test methods" describes the directions for determining the properties of the superabsorbers.

Test methods

1. Retention (TB)

The retention is measured according to the method described in EP 514 724 (page 4, lines 6–22).

2. Liquid Absorption under Pressure (AUP)

The liquid absorption under pressure (AUP at 0.3 and 0.7 psi, corresponding to 21 $g/cm^2$ and 49 $g/cm^2$, respectively) is determined according to the method described in U.S. Pat. No. 5,314,420, page 9, line 28ff; 0.9% common-salt solution is used as measuring liquid.

3. Soluble Constituents (SC)

The soluble constituents (1 h and 16 h) are determined as described in U.S. Pat. No. 4,654,039, except that a 0.9% common-salt solution is used as test liquid instead of synthetic urine.

4. Swell rate (SR)

The swell rate (SR) of the polymer is measured according to the following method: Twenty (20) grams of a synthetic urine solution (prepared according to U.S. Pat. No. 4,654,039) are weighed into a narrow beaker. One (1) gram of the material to be tested is measured into the middle of a broad (5 cm in diameter) cylindrical dish. The powder having the superabsorbent properties is uniformly distributed over the bottom of the dish by slight shaking. The synthetic urine solution is added in one shower by means of a hopper ending 1 cm above the bottom of the dish; this starts the time measurement. Measurement of time is terminated as soon as there is no liquid any longer.

EXAMPLES

Example 1

Reaction of Allyl Alcohol With 5 Moles of Ethylene Oxide 464.8 g allyl alcohol (Merck) is prepared together with 4 g sodium methylate solution (25%) in a 5-l-autoclave equipped with lifting agitator, and is freed from oxygen by introducing nitrogen five times up to 5 bar and subsequent release to 1 bar. With continued passage of nitrogen, the reactor content is heated to 70° C., removing the methanol brought in by the catalyst. After that, the reactor is closed, heated to 140° C., and at a total pressure of 3–6 bar, 1760 g ethylene oxide is introduced within 30 minutes. 2210 g light yellow liquid is obtained as product. The characteristics are listed in Table 1.

Example 2

Reaction of Allyl Alcohol With 10 Moles of Ethylene Oxide 290.5 g allyl alcohol (5 mol) is prepared together with 2.5 g solid KOH (85%) and rendered inert as in Example 1. 2200 g ethylene oxide (50 mol) is introduced within one hour at 4–6 bar and a reaction temperature of 140° C. 2480 g light yellow liquid is obtained as product. The characteristics are listed in Table 1.

Example 3

Reaction of Allyl Alcohol With 20 Moles of Ethylene Oxide 1495.8 g (3 mol) of the product of Example 2 is prepared in the five-liter-autoclave, rendered inert according to the procedure of Example 1, and reacted with 1320 g (30 mol) ethylene oxide within 1 hour at 140° C. 2805 g of a yellow solid is obtained. The characteristics are listed in Table 1.

TABLE 1

| Characteristics of the produced ethoxylates | | | |
|---|---|---|---|
| Product | Example 1 | Example 2 | Example 3 |
| OH number | 204 mg KOH/g | 118 mg KOH/g | 53 mg KOH/g |
| iodine number (Wijs) | 91 mg KOH/g | 53 mg KOH/g | 27 mg KOH/g |
| allyl alcohol (GC) | 2030 ppm | 144 ppm | 14 ppm |
| set. point | −15° C. | 3° C. | 29° C. |
| iodine color value | 3 | 7 | — |
| density | 1.054 g/ml | 1.085 g/ml | — |
| viscosity RV 2/10 | 18 mPas (20° C.) | 68 mPas (20° C.) | — |

Example 4

Acrylic Acid Ester of 10-EO-allyl Alcohol AAA-10

245 g (0.726 mol) 10-EO-allyl alcohol of Example 2 is stirred at 20° C. together with 155.6 g (2.16 mol) acrylic acid and 0.8 g p-methoxyphenol until the p-methoxyphenol has completely dissolved. Subsequently, 2.2 g sulfuric acid is added, and the batch is heated to 90° C. at a pressure of 800 mbar. A uniform air current is introduced into the batch via a gas frit. When 90° C. is achieved, the vacuum is increased to 400 mbar whereupon the batch starts to distill. After about 3–4 hours, the flow of distillate is exhausted, and the vacuum is improved to 100 mbar to complete the reaction. After 2 more hours, the batch is cooled and taken off. 451 g of a light yellow oil is obtained. Acid number: 69.1 mg KOH/g, saponification number: 175.6 mg KOH/g, degree of esterification: 99%.

Example 5

Acrylic Acid Ester of 5-EO-allyl Alcohol AAA5

275 g (1 mol) 5 EO allyl alcohol of Example 1, 0.8 g p-methoxyphenol, 216.3 g (3 mol) acrylic acid, and 2.0 g sulfuric acid are reacted as in Example 4. 385 g yellow oil is obtained. Acid number: 76.5 mg KOH/g, saponification number: 237.4 mg KOH/g, degree of esterification: 94.5%.

Example 6

Acrylic Acid Ester of 20 EO-allyl Alcohol AAA20

445.3 g (0.42 mol) 20-EO-allyl alcohol of Example 3, 0.8 g p-methoxyphenol, 21 6.4 g (3 mol) acrylic acid, and 2.0 g sulfuric acid are reacted as in Example 4. 547 g of a yellow red wax is obtained. Acid number: 68.5 mg KOH/g, saponification number:

126.1 mg KOH/g, degree of esterification: 97%.

Example 7

Methacrylic Acid Ester of 20-EO-allyl Alcohol MAA20

445.3 g (0.42 mol) 20-EO-allyl alcohol of Example 3, 0.8 g p-methoxyphenol, 385 g (4.53 mol) methacrylic acid, and 4 g conc. sulfuric acid are reacted as in Example 4, the reaction time being doubled and the vacuum at the end of the reaction being increased to 20 mbar. 555 g solid product is obtained. Acid number: 103.5 mg KOH/g, saponification number: 158.3 mg KOH/g, degree of esterification: 93.9%.

Example 8

Methacrylic Acid Ester of 5 EO-allyl Alcohol, MAA5

275 9 (1 mol) 5-EO-allyl alcohol of Example 1 is reacted as in Example 7 together with 0.8 g p-methoxyphenol, 516.6 g methacrylic acid (6.08 mol), and 2 g conc. sulfuric acid. A yellow liquid is obtained. Acid number: 98.1 mg KOH/g, saponification number: 247.8 mg KOH/g, degree of esterification: 91.6%.

Example 9

Methacrylic Acid Ester of 10 EO-allyl Alcohol, MAA10

479.5 g (1.01 mol) 10-EO-allyl alcohol of Example 2, 0.8 g p-methoxyphenol, 258.3 g (3.04 mol) methacrylic acid are reacted as in Example 7. 680 g of a yellow oil is obtained. Acid number: 99.5 mg KOH/g, saponification number: 196.0 mg KOH/g, degree of esterification: 94%.

The polymerization batches described in the following (Examples 10–17 and Comparative Examples C1–C5) are manufactured according to the following general method:

a) Starting product

In a cylindrical plastic vessel, a monomer solution is prepared consisting of 265.2 g acrylic acid and 372.4 g demineralized water as well as the used cross-linking agents. Under stirring and cooling, partial neutralization is carried out with 206.1 g 50% sodium hydroxide solution (neutralization degree 70%). The solution is cooled to 7–8° C., and nitrogen is bubbled through until the oxygen content in the monomer solution has dropped to a value of below 0.2 ppm. Subsequently, 0.3 g azo-bis(2-amidinopropane) dihydrochloride, dissolved in 10 g demin. water, 0.05 g sodium persulfate, dissolved in 6 g demin. water, 0.005 g hydrogen peroxide (35%), dissolved in 1 g demin. water, and 2 g sodium carbonate are added. Polymerization is then started by adding 0.012 g ascorbic acid, dissolved in 2 g demin. water, whereupon the temperature rises considerably. After that, the polymer is minced, dried at 140° C. in a circulating air drying cabinet, ground, and screened out to the grain fraction of 150–850 $\mu$m.

Example 18 and Comparative Examples C6–C10 are polymerized according to the above-mentioned general production direction; however, without addition of sodium carbonate.

b) Secondary cross-linkage:

100 g of the ground polymer screened out to 150–800 mm is wetted under intense mixing with a solution of 0.5 g ethylene carbonate and 1.5 g demin. water in a mixer of MTI, and then heated for 30 minutes to a temperature of 180° C. in an oven.

The Table in appendix 1 shows the composition and properties of the polymers according to Examples 10–18 and those of Comparative Examples C1–C10.

The Table shows that Examples 10–18 according to the present invention provide polymers having a combination of good properties:

| | |
|---|---|
| retention | >30 g/g and |
| absorption under pressure (21 g/cm$^2$) | >30 g/g and |
| absorption under pressure (49 g/cm$^2$) | >20 g/g and |
| swell rate | <40 s and |
| soluble constituents (16 h) | <12%. |

In the Comparative Examples it was possible to achieve single properties by varying the amount of cross-linking agent, but it was not possible to obtain the combination of these good properties.

Thus, depending on the amount used (C2 and C4), the Craynor 435-cross-linking agent (corresponding to WO 93/21237 and WO 94/9043) provides either products with a good AUP (49 g/cm$^2$) of 26.7 g/g and acceptable soluble contents but with a bad retention, or a product having a good retention and acceptable AUP but with a bad result concerning soluble constituents. All products with only one cross-linking agent have a bad swell rate despite the addition of sodium carbonate.

The cross-linker combination of trimethylolpropane triacrylate and triallylamine according to Comparative Example C6 is mentioned as a preferred combination in U.S. Pat. No. 5,314,420. The results demonstrate that neither retention, nor swelling rate, nor soluble contents achieve the properties of the polymers according to the present invention.

The experiments without added sodium carbonate (Example 18, C8–C10) demonstrate that the polymers according to the present invention retain their excellent property profile, i.e., as compared to the art, the improved swell rate does not depend on this component. Without added sodium carbonate the Comparative Examples show worse properties.

Examples: Use of the combination of cross-linker I and II according to the present invention

| Example | Cross-linker I | Amount | mmol | Cross-linker II | Amount | mmol | Retention | AUP (21 g/cm$^2$) | AUP (49 g/cm$^2$) | SR | SC |
|---|---|---|---|---|---|---|---|---|---|---|---|
| Examples. Use of the combination or cross-linker I and II according to the present invention | | | | | | | | | | | |
| 10 | AAA-10EO (Ex. 4) | 0.53 g | 0.96 | SR 351 | 0.27 g | 1.03 | 30.4 g/g | 32.9 g/g | 21 g/g | 34 s | 11.70% |
| 11 | AAA-10EO (Ex. 4) | 1.06 g | 1.92 | SR 351 | 0.14 g | 0.52 | 30 g/g | 33 g/g | 24.8 g/g | 30 s | 10.20% |
| 12 | AAM-10EO (Ex. 9) | 1.06 g | 1.99 | SR 351 | 0.14 g | 0.52 | 32.2 g/g | 33.0 g/g | 25.9 g/g | 33 s | 11.70% |
| 13 | AAA-5E0 (Ex. 5) | 1.06 g | 3.38 | SR 351 | 0.14 g | 0.52 | 31.6 g/g | 31.1 g/g | 25 g/g | 38 s | 10.40% |
| 14 | AAA-20EO (Ex. 6) | 1.06 g | 1.1 | SR 351 | 0.14 g | 0.52 | 31.1 g/g | 31.3 g/g | 23.7 g/g | 38 s | 11.00% |
| 15 | AAM-5EO (Ex. 8) | 1.06 g | 3.34 | SR 351 | 0.14 g | 0.52 | 31.0 g/g | 31.4 g/g | 22.5 g/g | 39 s | 10.20% |
| 16 | AAM-20EO (Ex. 7) | 1.06 g | 1.11 | SR 351 | 0.14 g | 0.52 | 31.4 g/g | 30.5 g/g | 24.2 g/g | 35 s | 9.50% |
| 17 | AAA-10EO (Ex. 4) | 0.53 g | 0.96 | CN 435 | 0.54 g | 0.615 | 32.6 g/g | 34.5 g/g | 26.1 g/g | 34 s | 9.30% |
| 18 | AAA-10EO (Ex. 4) | 0.2 | 0.36 | SR 351 | 0.27 g | 0.31 | 35.4 g/g | 33.5 g/g | 25.8 g/g | 38 s | 9.30% |
| Comparative Examples using only one cross-linker | | | | | | | | | | | |
| C1 | SR351 | 0.34 g | 1.32 | | | | 30.9 g/g | 27.8 g/g | 22.4 g/g | 59 s | 15.80% |
| C2 | CN 435 | 0.53 g | 0.62 | | | | 33.3 g/g | 35.6 g/g | 14.9 g/g | 56 s | 17.20% |
| C3 | triallylamine | 0.18 g | 1.31 | | | | 32.9 g/g | 28.4 g/g | 17.0 g/g | 54 s | 18.70% |
| C4 | CN 435 | 1.06 g | 1.23 | | | | 25.4 g/g | 23.9 g/g | 26.7 g/g | 56 s | 14.30% |
| C5 | AAA-10EO (Ex. 4) | 1.06 | 1.99 | | | | 36.0 g/g | 34.8 g/g | 20.2 g/g | 61 s | 15.50% |
| C8 | triallylamine | 0.48 g | 3.49 | | | | 33.0 g/g | 29.9 g/g | 12.0 g/g | 78 s | 25.00% |
| C9 | triallylamine | 0.76 g | 5.53 | | | | 30.4 g/g | 30.0 g/g | 20.6 g/g | 67 s | 16.50% |

-continued

| Example | Cross-linker I | Amount | mmol | Cross-linker II | Amount | mmol | Retention | AUP (21 g/cm²) | AUP (49 g/cm²) | SR | SC |
|---|---|---|---|---|---|---|---|---|---|---|---|
| Comparative Examples using two cross-linkers outside the combination according to the present invention | | | | | | | | | | | |
| C6 | triallylamine | 0.4 g | 2.91 | SR 351 | 0.13 g | 0.15 | 28.4 g/g | 31.2 g/g | 22.5 g/g | 45 s | 16.20% |
| C7 | allyl methacrylate | 0.53 g | 4.21 | CN 435 | 0.54 g | 0.615 | 25.4 g/g | 30.2 g/g | 25.0 g/g | 53 s | 6% |
| C10 | AAA-10EO (Ex. 4) | 0.4 g | 0.74 | triallylamine | 0.53 g | 3.86 | 27.8 g/g | 25.8 g/g | 23.3 g/g | 54 s | 11.50% |

SR 351: trimethylolpropane triacrylate of Cray Valley
CN 435: trimethyolpropane-15EO-triacrylate of Cray Valley

I claim:

1. A cross-linked polymer which absorbs aqueous liquids prepared by:
   (co)polymerizing (i) at least one partially neutralized, monoethylenically unsaturated, acid group-containing monomer or (ii) at least one partially neutralized, monoethylenically unsaturated, acid-group-containing monomer with a copolymerizable monomer or (iii) graft (co)polymerizing monomer(s) (i) or monomer combination (ii) onto a graft base in the presence of a cross-linking agent combination consisting of:

40–90 mol. % of $CH_2=CR^5-CO-(OCHR^3-CHR^3)_zO-CH_2-CR^5=CH_2$     (I)

and

10–60 mol. % of $R^1-[O(CHR^3-CHR^3O)_u-CO-R^2]_x$     (II)

wherein $R^1$ is a multivalent $C_{2-10}$-alkyl group, $R^2$ is a linear or branched $C_{2-10}$-alkenyl group, $R^3$ is H, $CH_3$ or $C_2H_5$, $R^5$ is H or $CH_3$, x is 2–6, u is 0–15 and z is 3–20, and a surface cross-linking agent.

2. The polymer according to claim 1 wherein 50–80 mol-% of cross-linking agent I is used and 20–50 mol-% of cross-linking agent II is used, relative to the cross-linker mixture.

3. The polymer according to claim 1 wherein 60–80 mol-% of cross-linking agent I is used and 20–40 mol-% of cross-linking agent II is used, relative to the cross-linker mixture.

4. The polymer according to claim 1 wherein the cross-linker combination is used in an amount of 0.1–2.0%-wt., relative to the monomers.

5. The polymer according to claim 1 wherein the cross-linker combination is used in an amount of 0.3–1.0%-wt., relative to the monomers.

6. The polymer according to claim 1 wherein cross-linker I in the polyglycol chain consists in weight average of at least 3 glycol units.

7. The polymer according to claim 1 wherein the unsaturated acid groups-containing monomers are selected from the group consisting of acrylic acid, methacrylic acid, vinyl acetic acid, vinyl sulfonic acid, methallyl sulfonic acid, and 2-acrylamido-2-methylpropane sulfonic acid.

8. The polymer according to claim 1 wherein it comprises incorporated by polymerization 0 to 40%-wt., relative to the acid groups-containing monomers, of further comonomers of the group consisting of (meth)acrylamide, (meth) acrylonitrile, vinyl pyrrolidone, hydroxyethyl acrylate, and vinyl acetamide.

9. The polymer according to claim 1 wherein it comprises 0 to 30%-wt., relative to the sum of all monomers, of water-soluble polymers suitable as a graft basis.

10. The polymer according to claim 1 wherein the secondary cross-linkage is optionally repeated several times.

11. The polymer according to claim 10 wherein it has been cross-linked at the surface with a secondary cross-linker belonging to the group of polyols, polyepoxides, polyamines, or alkylene carbonates.

12. The polymer according to claim 10 wherein has a retention of at least 30 g/g, a liquid absorption under pressure (49 g/cm2) of at least 20 g/g, a maximum of soluble constituents after 16 hours of 12%, and a swell rate of below 40 sec.

13. The polymer according to claim 1 wherein it has a liquid absorption under pressure (49 g/cm2) of at least 22 g/g.

14. The polymer according to claim 1 wherein it has a swell rate of below 35 sec.

15. The polymer according to claim 1 wherein the maximum of soluble constituents after 16 hours amounts to 10%.

16. The process according to claim 1 characterized in that surface treatment and cross-linkage are carried out several times.

17. A process for the production of a cross-linked polymer which absorbs aqueous liquids according to claim 1, comprising:

(co)polymerizing at least one unsaturated, acid group-containing, partially neutralized monomer and a cross-linking agent mixture of:

40–90 mol. % $CH_2=CR^5-CO-(OCHR^3-CHR^3)_zO-CH_2-CR^5=CH_2$     (I)

and

10–60 mol. % of $R^1-[O(CHR^3-CHR^3O)_u-CO-R^2]_x$     (II)

wherein $R^1$ is a multivalent $C_{2-10}$-alkyl group, $R^2$ is a linear or branched $C_{2-10}$-alkenyl group, $R^3$ is H, $CH_3$ or $C_2H_5$, $R^5$ is H or $CH_3$, x is 2–6, u is 0–15 and z is 3–20 in the presence of a radical generating agent in solution or in suspension thereby forming a hydrogel;

comminuting, drying, grinding and screening the polymer material obtained; and treating the polymer with a surface cross-linking agent at an elevated temperature.

18. The polymer according to claim 6, wherein the weight average of said cross-linker I in the polyglycol chain ranges from 5–20.

19. The polymer according to claim 18, wherein said range is from 8–12.

20. The polymer according to claim 9, wherein said graft base is a polysaccharide.

21. The polymer according to claim 9, wherein said graft base is polyvinyl alcohol.

22. A method of absorption, comprising:

contacting water, an aqueous liquid or body fluid with the cross-linked polymer of claim 1 which is a component of a device which comes into contact with water, an aqueous liquid or body fluid.

23. A method of supporting fertilizer or an active substance which is released in the environment, comprising:

supporting certain fertilizer or other active substance on the cross-linked polymer of claim 1, thereby providing for the prolonged release of said fertilizer or other active substance over a period of time.

\* \* \* \* \*